Figure 1:
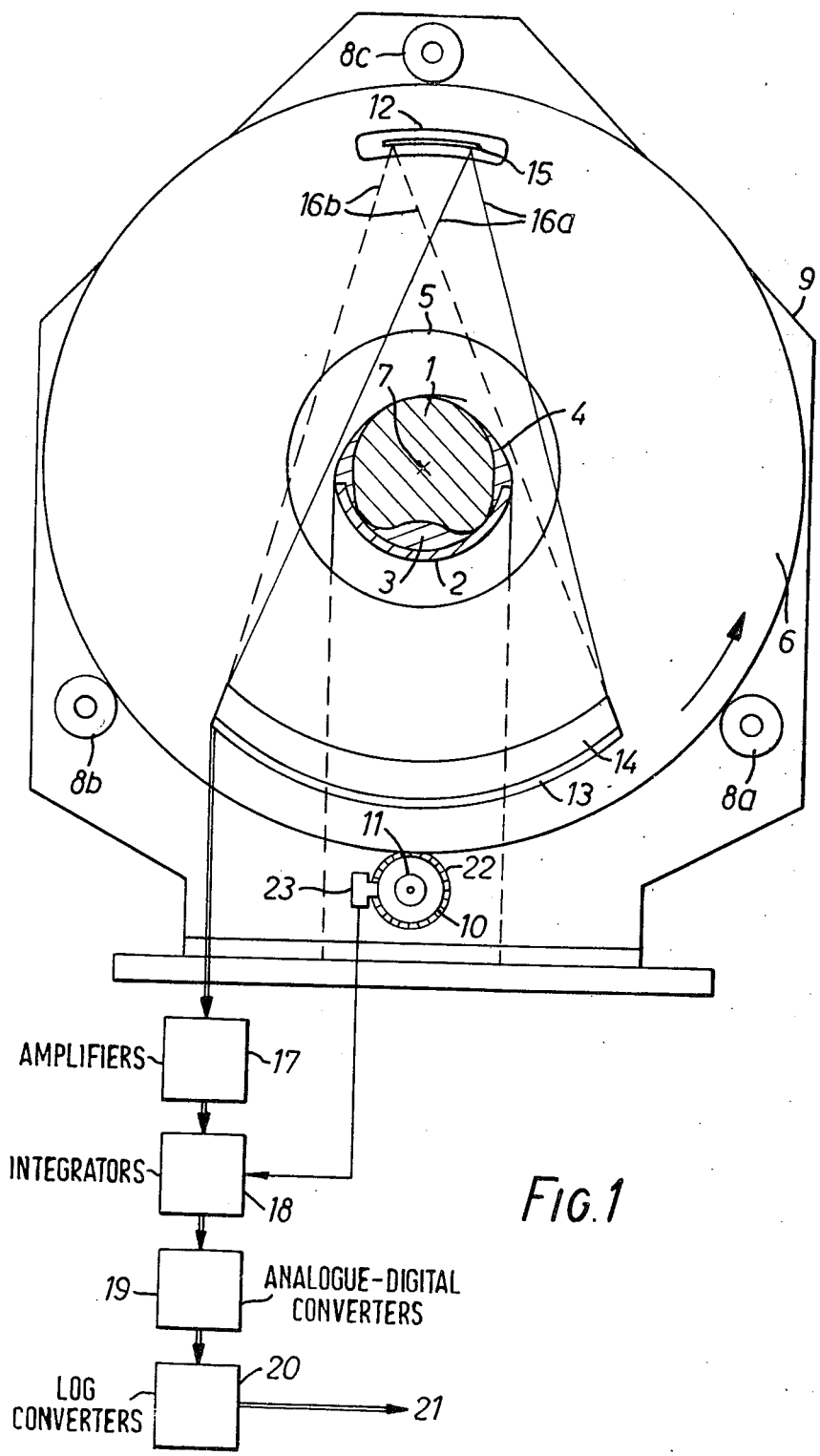

United States Patent [19]
Hounsfield

[11] 4,115,698
[45] Sep. 19, 1978

[54] RADIOGRAPHY

[75] Inventor: Godfrey Newbold Hounsfield, Newark, England

[73] Assignee: EMI Limited, Middlesex, England

[21] Appl. No.: 733,941

[22] Filed: Oct. 19, 1976

[30] Foreign Application Priority Data

Oct. 25, 1975 [GB] United Kingdom ............... 43984/75

[51] Int. Cl.² .............................................. G03B 41/16
[52] U.S. Cl. .................................. 250/445 T; 250/360
[58] Field of Search ............... 250/439 R, 444, 445 R, 250/445 T, 446, 490, 360, 363 R

[56] References Cited

U.S. PATENT DOCUMENTS 4,002,917  1/1977  Mayo .............................. 250/445 T

*Primary Examiner*—Craig E. Church
*Attorney, Agent, or Firm*—Cooper, Dunham, Clark, Griffin & Moran

[57] ABSTRACT

Radiographic apparatus is described for evaluating the absorption coefficient of a body at each of a plurality of locations distributed over a slice of a body. A source is arranged to produce a fan-shaped beam of radiation which is directed through the body and the source is orbited around the body about an axis intersecting the slice. Detectors are provided, and orbited in synchronism with the orbital motion of the source, each to detect the radiation emergent from the body along a plurality of paths. A lateral scan is imposed on the source relative to the detectors, the scan being repetitive so that, during each scan, each detector receives radiation along a plurality of mutually inclined beam paths. The beam paths thus examined are sufficient in number and distribution to allow the construction of composite measurements for a plurality of sets of composite, parallel beam paths distributed over the slice for processing to derive a representation of absorption coefficients for the slice.

7 Claims, 6 Drawing Figures

RADIOGRAPHY

This invention relates to a method of and apparatus for constructing a representation of the variation of absorption with position across a planar slice of a body with respect to penetrating radiation such as X- or γ-radiation.

One method of and apparatus for constructing such a representation is described in U.S. Pat. No. 3,778,614. According to one example given in that specification, a scanning movement is imparted to a suitable source of radiation to provide a plurality of substantially parallel pencil beams of radiation at each of a plurality of inclinations in the plane of the slice. A suitable detector is scanned in a corresponding manner to provide a measure of the absorption suffered by each of the beams in passing through the body. These measurements of absorption are then processed by a method involving successive approximations to provide a distribution of linear absorption coefficients for the planar slice. To provide the required plurality of beams, the source and detector are reciprocated in the plane of the slice and orbited in steps about a common axis normal to that plane.

An alternative processing method involving a form of convolution is further described in U.S. Pat. No. 3,924,129.

The method and apparatus described in the said U.S. Pat. No. 3,778,614 has proved to be successful for producing cross-sectional representations of parts of a living body such as the head. However the arrangement for carrying out the scanning operation is relatively slow and a faster scanning rate is desirable for certain parts of the body. U.S. Pat. No. 3,937,963 describes a method of and apparatus for constructing the said representation of absorption including a scanning arrangement arranged to direct a fan shaped spread of X-rays through the body and providing a plurality of detectors distributed across the fan on the other side of the body to measure the radiation transmitted along a set of beams within that spread. The fan shaped spread subtends an angle sufficient to include the whole region of interest in the plane of the body so that a complete scan can be effected solely by orbiting the source and detectors about a suitable axis.

The apparatus described in the said U.S. Pat. No. 3,937,963 can suffer from difficulties arising from errors which are introduced into the finally derived representation by virtue of differences of sensitivity between the plurality of detectors used. It is, therefore, preferable to provide means for equalising the sensitivities of the detectors.

It is an object of the present invention to provide an alternative form of its said apparatus for which the said sensitivity differences can be more readily corrected.

According to the invention there is provided radiographic apparatus comprising: means defining a patient position; a source of a substantially planar, fan-shaped spread of X-radiation; means supporting said source so that said radiation propagates through a region of said patient position along a plurality of diverging beam paths; detecting means, also supported by said supporting means, including a plurality of detector devices each adapted to detect radiation emergent from said region along a respective one of said beam paths; scanning means for moving said supporting means and with it said source and said detecting means, angularly, around said patient position causing said source to project said radiation through said region along further beam paths and causing said detecting means to detect radiation emergent from said region along said further beam paths, each detector device producing distinguishable electrical signals relating to a plurality of said beam paths during movement of said support through a substantial angle; means causing the source of said spread of radiation to repeatedly shift with respect to said detecting means during said angular movement through said substantial angle so that each detector device detects sequentially, during each shift, radiation emerging from said region along several mutually inclined beam paths; and means for combining electrical signals produced by different detector devices for beam paths which pass through substantially the same part of said region to provide composite electrical signals, each of which relates to a composite beam passing through said part of the region, for processing to derive a representation of the distribution of absorption of the radiation in said region.

Figure 2:
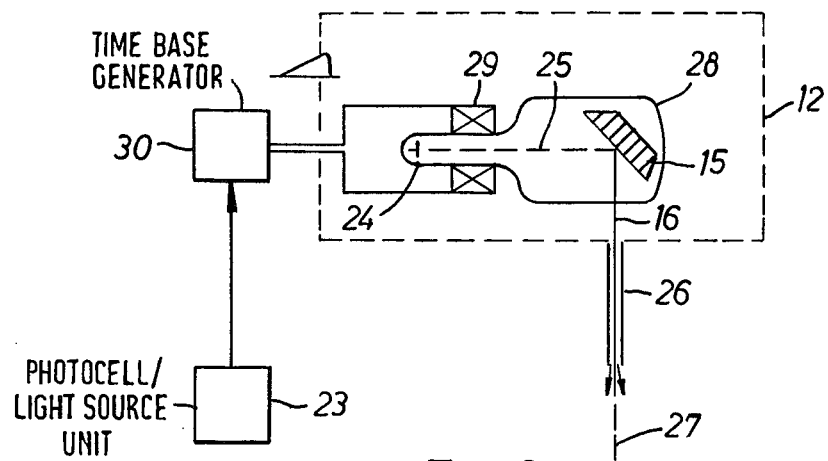
Figure 3:
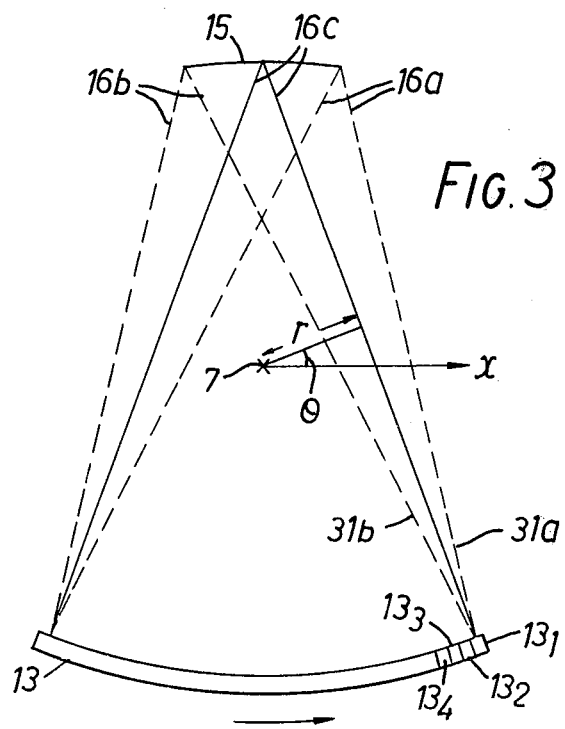
Figure 4:
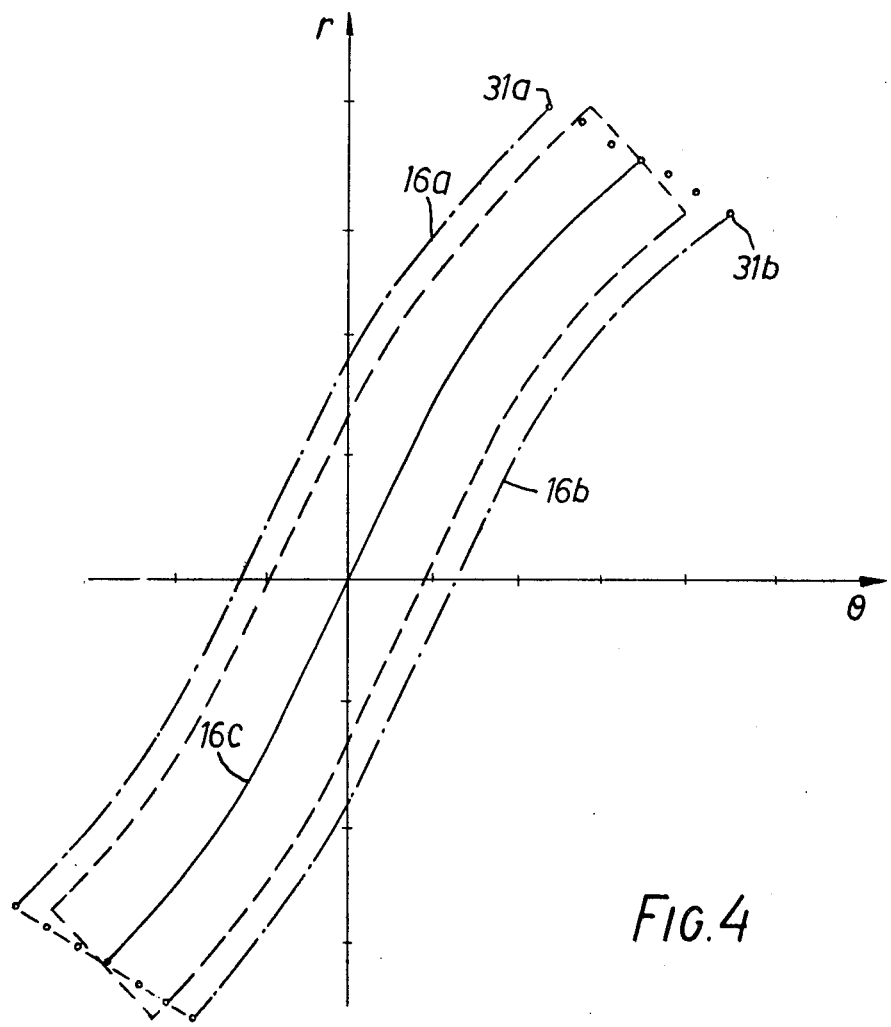
Figure 6:
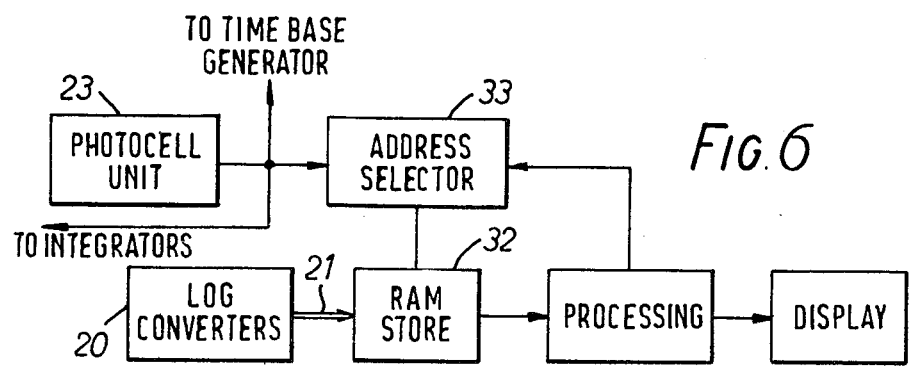
Figure 5:
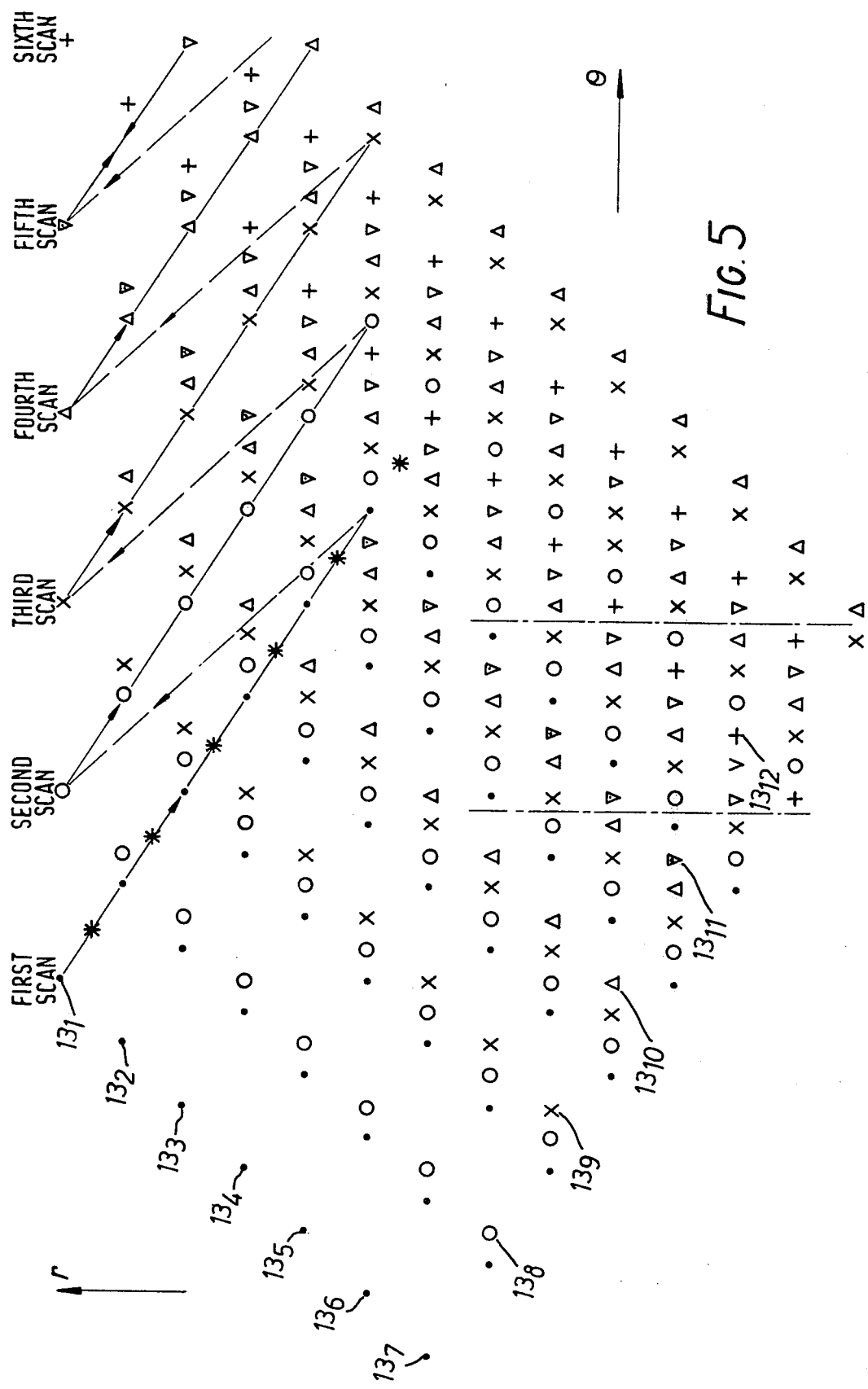

In order that the invention may be clearly understood and readily carried into effect one example thereof will now be described with reference to the accompanying drawings of which, FIG. 1 shows an apparatus in accordance with one example of the invention, FIG. 2 illustrates an X-ray source for use with the invention, FIG. 3 is a simplified diagram illustrating the scanning of the apparatus shown in FIG. 1, FIGS. 4 and 5, are explanatory diagrams used to explain the relationship between the relative motions of the apparatus in accordance with the invention and FIG. 6 shows in block diagrammatic form circuits for arranging the output data for processing.

Referring to FIG. 1, there is shown in front elevation apparatus in accordance with one example of the invention. A body 1 to be examined, shown in transverse section, is supported on a suitably shaped bed 2 also shown in transverse section.

A material 3, having an absorption to the radiation similar to that of body tissue, is positioned between the body 1 and bed 2 to substantially exclude air from the gap therebetween and to provide some support for the patient and is extended partly about the body, to provide an approximately circular cross-section to the radiation. The material 3 may be water or a viscous or particulate material in one or more flexible bags. The body is retained firmly in the desired position by means such as a retaining strap 4.

The bed 2 and the body 1 are inserted into an opening 5 in a rotatable member 6 so that a desired part of the body is centred in the opening. The rotatable member 6 is arranged to rotate about an axis 7, longitudinal of the body and perpendicular to the paper, intersecting the opening 5. For that purpose it is supported by three gear wheels 8, a.b.c. which engage with gear teeth, not shown, cut into the periphery of member 6. The gear wheels 8 are journalled in a main frame 9 of the apparatus, which may take any form suitable to support the apparatus and to allow the necessary rotation. A further gear wheel 10 also engaging with the said gear teeth, is driven by an electric motor 11, also mounted on the main frame 9, and serves to provide the required rotary motion.

The rotatable member 6 also carries a source 12 of X-rays, a bank of detectors 13 and associated collimators 14. The detectors, which in a typical embodiment number 240, can be of any suitable type, for example scintillation crystals with associated photomultipliers or photodiodes.

The source 12 is of the type which includes an elongated target/anode 15, which will be discussed further hereinafter, and provides a fan shaped beam 16 of X-rays from a substantially point origin which can be scanned by electronic means from the position 16a to the position 16b shown. In this example the fan of X-rays extends over 40° and the scan of the substantially point origin of the X-rays along target 15 is of the order of 10 cm although it may be less if desired. The collimators have longitudinal axes which intersect at the centre of the anode 15. The detectors are arranged to intercept the radiation of fan 16 for any position of the point of origin of the X-rays in its lateral scan along target 15. It should be understood that collimators 14 are of dimensions which allow such interception while preventing the reception of scattered radiation to the greatest degree practically possible.

In this example the X-ray source 12 is placed of the order of 50 cm from the central axis 7 with the detector 13 being placed a further 50 cm on the opposite side of axis 7. If desired however the distances from source to axis 7 and detectors to axis 7 may be unequal, without departing from the principles of the invention, provided the geometry of the arrangement is accurately known.

Disregarding for the moment the rotary motion referred to hereinbefore, the arrangement is such that the point of origin of the X-rays is scanned steadily along target 15 taking the fan of X-rays from 16a and 16b, and is rapidly returned to the starting point before repeating the scan. During the time of one such scanning movement each detector of array 13 provides an output signal indicative of the intensity of radiation incident thereon. These output signals are amplified in amplifiers 17 and then input to integrators 18. Each output signal is then integrated over a period chosen so that it provides an analogue signal representing the total intensity of radiation incident on the respective detector during that time and transmitted through the body 1 along a path effectively, examined by that detector taking into account the rotational motion. In this example, for the sake of more clearly illustrating the relationships involved, the timing of the integration interval will be considered to be suitable to provide seven periods in the time of one lateral scan of X-ray fan 16 from 16a to 16b. It will be understood that in practice a larger number, typically fifty, of integration intervals would be provided for one scan. The arrangement of this example ensures therefore that each detector measures radiation, in effect, along seven narrow beam paths joining that detector with seven equally spaced positions along target 15. The paths are, of course, of widths determined by the integration intervals and static beam geometry and are of a shape determined by the geometry of scanning movements in those intervals. For the purpose of illustration, however, they may be considered to be represented by single lines which are in fact their centre lines. The lines illustrating the extremes of fan 16 are thus the centre lines of the extreme beams of the fan.

The analogue signals for those paths are then converted to digital form in converters 19 and to logarithmic form in converters 20 for output at 21 to further processing. It will be understood that one amplifier 17, integrator 18, A/D converter 19 and log converter 20 is provided for every detector, all operated in synchronism. All of the circuits 15 to 19 are of well known construction. The processing is effective to sort the signals into sets representing absorption along sets of parallel paths, as will be further explained hereinafter, for processing by a suitable method, such as that described in U.S. Pat. No. 3,924,129 to provide the desired representation.

In order to achieve the effect of the present invention, which will be described in detail hereinafter, the motor 11 provides a continuous motion of rotatable member 6 and all the equipment mounted thereon, about axis 7 and therefore about the body 1 of the patient on bed 2. The motion and the lateral scanning of X-ray fan 16 must be in strict relationship to achieve the desired result. For this purpose the shaft of gear wheel 10 has mounted co-axially thereon a circular graticule 22 in the form of a translucent ring carrying radial engraved lines. The lines can interrupt a light path between a light source and photocell in a unit 23 mounted on frame 9, so that the photocell provides pulses indicative of the rotary movement of member 6. These pulses may be used both to operate the integrators 18 and to control the X-ray source 12 as described hereinafter. It will be apparent that all paths of the radiation do not intercept equal lengths of the body 1, in view of the approximately circular cross-section of the body and any surrounding material. For this reason the outer detector of the array tend to give higher outputs than centrally disposed detectors, even for a body of uniform absorption. This effect may be reduced by providing suitably shaped attenuating bodies, not shown, between source 15 and body 1 and/or between body 1 and detectors 13 to substantially equalise the absorbing path lengths. Alternatively, the gains of the respective detectors and/or amplifiers may be suitably adjusted. Alternatively, or in addition correction factors may be measured in the presence of an artificial body of uniform absorption such as water in a suitably shaped box or a phantom of plastic material. Such correction factors may later be subtracted from the measured output signals for the body 1.

The X-ray source 12 is shown in greater detail in FIG. 2 and comprises an electron gun 24, powered by a conventional supply not shown, providing a beam of electrons 25 which is incident on target/anode 15 to provide X-ray fan 16. In FIG. 2 the elongation of target 15 is perpendicular to the paper so that the X-ray fan 16 is also perpendicular to the paper. Source collimator 26 is provided, as shown, to restrict the X-rays substantially to the plane of the fan, shown dotted at 27 and that is then the plane of a section of the body 1 to be examined. It will be understood however, that examination need not be restricted to a plane if this is not desired. The electron gun and target are enclosed in an evacuated envelope 28 having a neck section around which are disposed scanning coils 29 receiving a sawtooth signal from a time base generator 30. In operation the sawtooth voltage from generator 30 scans the point of incidence of the electron beam 25 along target 15 from one end in a direction perpendicular to the paper to scan the X-ray point of origin as shown in FIG. 1. Although a pencil beam of electrons is indicated it will be understood that it may be a ribbon shaped beam used in conjunction with a suitable shape of target 15. Furthermore oil cooling of target 15, although not shown, is preferably provided in a conventional manner. Although scanning coils have been shown in FIG. 2, deflection plates may be used if desired; any configuration of source 12 capable of achieving the scanning of the X-ray fan 16 being suitable for use with the invention.

As mentioned hereinbefore, time base generator 30 provides the scanning sawtooth voltage in conventional manner and to provide the desired scanning relationship this sawtooth is to be maintained in a correct phase with the rotation. The exact relationship used is determined by the pulses from photocell unit 23. Since the pulses are also supplied to integrators 18, the integration times are retained in the desired relationship with the scanning of X-ray fan 16 to provide the required effective beam paths.

It has been mentioned that processing, suitable for use with X-ray apparatus of the type described, such as that disclosed in said U.S. Pat. No. 3,924,129 operates preferably on data representing the absorption along a plurality of sets of parallel beam paths in the plane of examination. The present invention provides such data while allowing correction for relative sensitivity differences between individual X-ray detectors used.

FIG. 3 illustrates the scanning arrangement in simplified form, disregarding the rotational motion of rotary member 6. Three fans of X-rays, 16a and b as in FIG. 1 and a further central fan 16, are shown emanating from target 15 and impinging on detectors 13. It will be seen that each beam, as defined by the position of its centreline, can be described uniquely by values of $r$ and $\theta$ where $r$ is the perpendicular distance from the centreline to the rotational axis 7 and $\theta$ is the angle between that perpendicular and an arbitrary $x$ direction. It will be understood that a set of parallel beam paths is a set having different values of $r$ and the same value of $\theta$. A plurality of such sets is to be provided at different values of $\theta$ as required by the processing referred to hereinbefore.

As mentioned, the integrator timing in this example is such that, as the point of origin of the X-rays is scanned from one end to the other of target 15, seven integration intervals occur, giving outputs representing seven beam paths for each detector. Thus detectors $13_1$, in FIG. 3 gives data for beam paths whose centrelines are equiangularly spaced between 31a and 31b.

FIG. 4 shows a graph representing the position of beam centrelines in terms of $\theta$ and $r$ for one lateral scan of fan 16. In $r/\theta$ diagrams such as FIG. 4, for the sake of clarity points representing beam paths will be identified by the reference numbers used in FIG. 1 or 3 to identify either the beam paths themselves or the detectors examining them. The two chain dotted lines are the loci of points representing the beams of fans 16a to 16b. Although it has been said that seven such fans are required from a seven position scan, one extreme fan may be omitted by virtue of an overlap which will be discussed hereinafter. One fan 16 is central to the arrangement and is represented by the solid line at 16c. The curvature of the lines given by 16a and 16c in FIG. 4 arises because $r$ does not vary linearly with $\theta$; there being a sinusoidal relationship between them. It will be understood that each such line is really a plurality of points, one for each detector, and that between each lies, in this example, two other equally spaced loci provided by the intervening integration intervals. FIG. 4 shows all of the individual points for the seven beam paths, from 31a to 31b, incident on detector $13_1$. The area of the diagram of FIG. 4 enclosed by these loci will be referred to hereinafter as a "patch", it being understood that each such "patch" is in fact a matrix of points representing the position in $r$ and $\theta$ of the individual beam paths provided by one lateral scan of the X-ray source 10.

The description so far has disregarded the rotational motion. The effect of a continuous rotational motion, during a source scan, on a patch is to distort it, in this example as shown by the broken lines. Those lines show the shape of a typical patch as achieved in practice and which will be assumed hereinafter. All other considerations relating to the patch are as described. It should be understood that although the shape of the patch indicated by broken lines is correct, its displacement relative to the non-rotational patch is determined by the arbitrary choice of a zero position for the rotational motion. In this example of FIG. 4 the rotational origin is set at the centre of the patch so that the new patch is displaced equally on oposite sides of the original one. In this example the lateral scan of the source point and the rotation of the source have been shown to be in the same direction (anticlockwise as shown in FIG. 3). It should however be understood that the lateral source scan and rotational motion may, if desired, be in opposite directions so as to cause distortion in the opposite sense to that shown in FIG. 4. Provided the relative timings are correct such opposite motion can readily be arranged to provide the same effective relationships.

The timing relationship between the lateral scan of the X-ray source and the rotational motion is, in accordance with the invention, arranged to satisfy two conditions. These can be seen in FIG. 5 which shows, at an arbitrary position to the $r/\theta$ diagram, the beam paths examined by some of the detectors $13_1$, $13_2$ etc. for six successive lateral scan positions. All of the integration intervals are indicated, by respective symbols which will be explained hereinafter, for three such scans and some positions for three more scans. At the start of one scan the first seven detectors, $13_1$, to $13_7$ provide data for the points indicated. The scan starting from those points will be labelled herein as the 'first scan' although it is to be considered typical of all and not necessarily from a starting position. It will be understood that data may already have been provided for other such positions starting to the left of the 'first scan' in FIG. 5.

In the course of, in this example, six integration intervals detector $13_1$ provides data for paths whose centrelines are indicated by the dots on the arrowed line. The other detectors provide data for the positions indicated by the other dots, moving through the same steps of $r$ and $\theta$ as $13_1$. For reasons to be explained hereinafter the sixth position is, in this example, the last of the patch and flyback then follows to take detector $13_1$ to the position at the start of the 'second scan' indicated by an open circle. The other detectors flyback to corresponding positions. It will be seen that these are at the same values of $r$ as at the start of the 'first scan' and are close to, but displaced in $\theta$ from, the second integration positions of the 'first scan'. Thus detector $13_2$ is now close to a position previously occupied by $13_1$ and detector $13_8$ has now entered the diagram to be close to an earlier position of $13_7$. In the course of the next lateral scan the detectors now provide data for beam path positions on the patch indicated by the open circles.

In successive lateral scans therefore detector $13_1$ follows the arrowed line, with flyback indicated by the arrowed broken line, while the detectors provide successive patches having beam path positions indicated by respectively diagonal crosses for the 'third scan', triangles for the 'fourth scan', inverted triangles for the fifth scan and vertical crosses for the sixth scan. Patches for further scans will of course be provided but have not been shown in FIG. 5.

The relationship of the flyback time of the source spot to the orbital motion is chosen to obtain a suitable displacement of successive patches which in this example ensures an even distribution of beam path positions in the diagram, as may be seen in the lower part of FIG. 5 in a region for which all patch points are shown. The relationship also provides that beam path positions lie in substantially vertical columns in the diagram to provide sets at constant $\theta$ which could be the data sets for parallel beam paths referred to hereinbefore. The even distribution and vertical columns are the two conditions referred to hereinbefore. However in an alternative example it could be arranged so that the flyback caused the beam paths to overlie paths previously scanned by other detectors instead of being close to them but displaced as described hereinbefore. In that alternative arrangement each beam path reading would be the sum of several readings for the identical path obtained by several different detectors.

In consideration of the relationships of the present example it will be seen that if a further integration interval before flyback had been provided for the 'first scan' indicated by dots, data would have been provided unnecessarily for positions later to be provided by the sixth scan, indicated by vertical crosses. The first patch is therefore terminated at the point shown to provide complete and unduplicated data. If desired it could be arranged to include this duplicated reading for the purposes of, for example, a check on the relative sensitivities of the two detectors.

Although the description so far has assumed that each position on the diagram represents a single beam path, in practice the detectors are closely spaced so that such beam paths would be relatively narrow. In the practical arrangement therefore the data for several positions at constant $r$ are combined to give composite beam paths each combining data from several detectors. This is illustrated at the lower part of FIG. 5 where data between the chain dotted lines are combined for each constant $r$ row to provide a constant $\theta$ column representing a set of parallel beam paths each one of which is associated with combined data from, in this example, six detectors. The $\theta$ positions of these beam paths will be taken at this midpoints which are considered to be midway between the chain dotted lines. Larger numbers of detectors may, of course, be combined as desired. It will be seen that the output signal for each beam path will be the combination of the output signals from a different distribution of detectors from different lateral scans thus distributing in successive output signals any errors due to sensitivity differences in the detectors. In view of the problems associated with providing collimators able to 'see' different positions of the source spot in its scan, further sensitivity differences, for a detector/collimator combination may be introduced dependant on the X-ray source spot position for any beam path. The differing distributions of detectors in the combinations referred to ensures that such further sensitivity differences are also distributed through data for each set of parallel paths so that errors introduced thereby are reduced.

As mentioned hereinbefore the paucity of data for beam path positions to the left of the diagram of FIG. 5 is due to the fact that earlier source scan data have not been shown in the Figure. However, it will be seen that at the top of the Figure the data for the extreme detectors of the array give gaps caused by the nature of the overlap. The same will be true of detectors at the other extreme. Since these gaps fill in less important regions at the extremes of the body the composite paths for those regions may be provided from reduced data without significant error to central regions. Alternatively the geometry may be arranged so that the missing data are for regions external to the body in which case they may be used merely to provide correction in the convolution processing or omitted entirely if desired.

In the arrangement assumed for FIG. 5 the integration invervals have been timed so that the successive beam path positions of a 'scan' have the same distribution in $r$ as the detectors. Further intermediate positions may be provided, however, and in one example these may be at the points indicated by asterisks for the first scan of detector $13_1$. Although other such positions have not been shown for clarity it will be seen that they would provide beam path positions intermediate in $r$ to those shown but in similar even distribution. In the example shown the flyback is delayed to provide a last position at the extreme lower right asterisk and is speeded up to commence the second scan as shown.

It will be seen that such intermediate path positions are also intermediate in $\theta$ thus providing a slight deviation in $\theta$ in the final parallel sets of data. However such deviation is small compared with the range of $\theta$ covered by the combination of data referred to hereinbefore and may be disregarded. Preferably the deviation is arranged to be at a relatively high spatial frequency as in the illustrated arrangement and does not take the form of a low frequency drift.

Although, as has been mentioned, the combination of data distributes sensitivity differences, thus reducing errors, the opportunity provided by the provision of data for closely spaced beam paths by different detectors, may be taken to correct for such sensitivity differences by relative adjustment of respective amplifier gains. Preferably, however, such adjustment should not be effected from single data values but from estimated sensitivities accumulated over a number of data values and constantly updated.

Considering FIG. 5 it will be readily apparent that the same desirable distribution of beam path positions can be obtained if the source spot scan and rotational motion are in opposite senses. Clearly certain relationships will be changed so that if, for example, the rotation is in the direction of positive $\theta$, the source scans will be in the direction of negative $\theta$ and the flyback the reverse. However the essential distribution can be arranged to be the same. It should also be noted that although the source and detectors have been shown equidistant from the axis, the distribution can also be adjusted by making these distances unequal.

The invention has been described in terms of an arrangement employing a complete 360° rotation of member 6. Although this results in the same beam paths being examined from opposite directions this may be desirable as scattering of the radiation tends to be different for 180° displaced detector positions and errors caused thereby are thus reduced. If desired, however, scanning over a smaller angular range may be employed, providing sufficient parallel sets for the processing used are obtained.

It will be understood that the ratios of the lateral scanning and rotational movements and the integration intervals are fixed for any particular example of the apparatus, as design parameters, although means for adjusting them may be provided if desired. Consequently the data provided by the detectors will be for a predetermined sequence of beam paths. Similarly the combination of data to provide the aforementioned composite beam path will be in a known predetermined manner. A suitable circuit is illustrated in block diagrammatic form in FIG. 6.

The photocell unit 23 provides a series of pulses at the same timing as the data signals and these are therefore used to clock the log converted signals at 20 in FIG. 1 into a random access memory (RAM) store 32 in predetermined locations in the correct sequence. The locations are determined by an address selector 33 which requires the clock pulses from the photocell unit. Each data signal is added to any data already in its respective location so that the multiple signals for each composite beam path are properly accumulated. For the reasons given it is known, for each beam path, how many signals have contributed to the data. Thus the total signals can be equalised suitably as they are read out in sets at constant $\theta$ for processing in processing circuits 34, for example, as described in the said U.S. Pat. No. 3,924,129. Circuits 34 request the data in sequence by sending suitable pulses to address selector 33 to initiate the prearranged output sequences. It will be understood that the transfer of information in response to suitable clock pulses is well known, for example, in the computer art and that the circuits illustrated here in block form may take any form desired by the designer of detailed circuits provided they assemble data signals in the correct sequences described hereinbefore.

In practice that processing requires data for a set of parallel beam paths substantially equally distributed across the body section being examined. As will be seen from the curved form of the patches, for example in FIG. 4, the sets obtained according to the present invention are not so equally distributed. Consequently correction should be made for the error. To this end, the data for sets of parallel beam paths are read out of the RAM store from the predetermined location and are then subject to interpolation to provide further sets of data applicable to notional beam paths which are properly equally distributed. The data for these notional sets are those used in the processing referred to. It will be understood that any suitable form of interpolation may be used to provide the equally distributed data.

It should be understood that the condition, referred to hereinbefore, that data are evenly distributed in $\theta$ for each value of $r$, is a convenience which allows ready combination as desired. The distribution need not, however, be uniform provided suitable allowance is made for the actual distribution in the processing.

What I claim is:

1. Radiographic apparatus comprising: means defining a patient position; a source of a substantially planar, fan-shaped spread of X-radiation; means supporting said source so that said radiation propagates through a region of said patient position along a plurality of diverging beam paths; detecting means, also supported by said supporting means, including a plurality of detector devices each adapted to detect radiation emergent from said region along a respective one of said beam paths; scanning means for moving said supporting means, and with it said source and said detecting means, angularly around said patient position causing said source to project said radiation through said region along further beam paths and causing said detecting means to detect radiation emergent from said region along said further beam paths, each detector device producing distinguishable electrical signals relating to a plurality of said beam paths during movement of said support through a substantial angle; means causing the source of said spread of radiation to repeatedly shift with respect to said detecting means during said angular movement of the supporting means though said substantial angle so that each detector device detects sequentially, during each shift, radiation emerging from said region along several mutually inclined beam paths; and means for combining electrical signals produced by different detector devices for beam paths which pass through substantially the same part of said region to provide composite electrical signals, each of which relates to a composite beam path passing through said part of the region, for processing to derive a representation of the distribution of absorption of the radiation in said region.

2. Radiographic apparatus according to claim 1 wherein said means causing said repeated shifts is arranged such that for each detector device at least some of the mutually inclined beam paths for which radiation is detected are substantially parallel to at least one of the mutually inclined beam paths for which radiation is detected by the other detector devices during the same shift.

3. Radiographic apparatus according to claim 1 wherein said means causing said repeated shifts is arranged such that for each detector device each of the mutually inclined beam paths for which radiation is detected during one of said shifts is substantially parallel to beam paths for which radiation is detected by detector devices, which may include the same detector device during others of said shifts.

4. Radiographic apparatus according to claim 1 wherein said means for causing said repeated shifts is arranged so that the angular displacements between successive beam paths relating to a detector device during a shift are of the same sense as the angular motion of the supporting means.

5. Radiographic apparatus according to claim 1 wherein the said scanning means and the said means for causing repeated shifts are arranged so that the beam paths for which the detector devices receive emergent radiation during each one of said shifts intersect a part of said region, which overlaps at least one part intersected by the corresponding beam paths during another shift.

6. Radiographic apparatus according to claim 1 including processing means arranged to process the said electrical signals or further signals derived therefrom to derive a representation of the distribution of absorption of the radiation in said region.

7. Radiographic apparatus according to claim 1 wherein the means for combining is arranged to combine electrical signals relating to a plurality of substantially coincident beam paths through the said region.

* * * * *